(12) United States Patent
Wada et al.

(10) Patent No.: US 9,709,566 B2
(45) Date of Patent: Jul. 18, 2017

(54) CHROMATOGRAPHY METHOD, AND CHROMATOGRAPHY KIT

(71) Applicant: FUJIFILM Corporation, Tokyo (JP)

(72) Inventors: Atsuhiko Wada, Ashigarakami-gun (JP); Ayumi Era, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 112 days.

(21) Appl. No.: 14/227,298

(22) Filed: Mar. 27, 2014

(65) Prior Publication Data

US 2014/0295405 A1    Oct. 2, 2014

(30) Foreign Application Priority Data

Mar. 28, 2013 (JP) .................................. 2013-068503
Feb. 28, 2014 (JP) .................................. 2014-038232

(51) Int. Cl.
*G01N 33/569* (2006.01)
*G01N 33/558* (2006.01)
*G01N 33/543* (2006.01)
*B01D 15/38* (2006.01)

(52) U.S. Cl.
CPC ... *G01N 33/56983* (2013.01); *B01D 15/3828* (2013.01); *G01N 33/54306* (2013.01); *G01N 33/558* (2013.01)

(58) Field of Classification Search
CPC ....... G01N 33/56983; G01N 33/54306; G01N 33/558; B01D 15/3828
See application file for complete search history.

(56) References Cited

U.S. PATENT DOCUMENTS

2009/0298050 A1*  12/2009  Katada ................. G01N 33/543
                                                                      435/5
2010/0113758 A1*   5/2010  Wilmer ................ C12N 15/101
                                                                      536/23.1

FOREIGN PATENT DOCUMENTS

| JP | 3-2662 A | 1/1991 |
| JP | 6-167499 A | 6/1994 |
| JP | 7-27765 A | 1/1995 |
| JP | 7-159406 A | 6/1995 |
| JP | 11-146783 A | 6/1999 |
| JP | 2009-216695 A | 9/2009 |

OTHER PUBLICATIONS

Machine translation of JPH06167499A, 10 pages.*
Machine translation JPH06167499, 9 pages.*
Japanese Office Action dated Jan. 27, 2015, for Japanese Application No. 2014-038232 with the English translation.
Extended European Search Report, dated Jul. 9, 2015, for European Application No. 14162320.7.

* cited by examiner

*Primary Examiner* — Andrea S Grossman
(74) *Attorney, Agent, or Firm* — Birch, Stewart, Kolasch & Birch, LLP

(57) ABSTRACT

The chromatography method of the present invention includes (a) developing a complex of a test substance and a labeling substance modified with a first binding substance bindable to the test substance, onto an insoluble carrier, (b) causing the complex to be trapped in a reaction site on the insoluble carrier which contains a second binding substance bindable to the test substance or a substance exhibiting binding properties to the first binding substance, (c) washing the insoluble carrier with a washing solution containing at least one of the potassium iodide, urea, and guanidine after the step (b), (d) washing off the washing solution of the step (c) remaining in the insoluble carrier from the insoluble carrier, and (e) amplifying the labeling substance of the complex trapped in the reaction site.

7 Claims, 4 Drawing Sheets

STRIP FOR CHROMATOGRAPHY

OUTSIDE

INSIDE

CHROMATOGRAPHY METHOD, AND CHROMATOGRAPHY KIT

BACKGROUND OF THE INVENTION

1. Field of the Invention

The present invention relates to a chromatography method and a chromatography kit which make it possible to detect an object analyzed with high sensitivity and at a high S/N ratio (ratio of signals to noise).

2. Description of the Related Art

Among immunoassays, an immunochromatography method is frequently used since this method can be handled easily and makes it possible to measure substances in a short time. As immune reactions used in the immunochromatography method, a competitive reaction and sandwich-type reaction are widely used. Among the reactions, the sandwich-type reaction is mainly used in the immunochromatography method, and typically, the following operation is performed to detect a test substance consisting of antigens in a sample. First, fine particles, which have been sensitized with antibodies against the antigens as the test substance, are immobilized in the form of solid-phase fine particles onto insoluble carriers, or alternatively, the aforementioned antibodies are directly immobilized onto insoluble carriers, whereby insoluble carriers having a reaction site where the antibodies react with the antigens as the test substance are formed. Meanwhile, fine labeling particles are sensitized with antibodies that can bind specifically to the test substance so as to prepare sensitized fine labeling particles. The sensitized fine labeling particles are made to move on the insoluble carriers together with the sample containing the test substance. By the above operation, the antibodies having been immobilized to the reaction site formed in the insoluble carriers function as an immobilized reagent, and the sensitized fine labeling particles bind specifically to the immobilized reagent via the antigens as the test substance. As a result, by determining whether there is a signal that is generated when the sensitized fine labeling particles are trapped in the reaction site or by judging the intensity of the signal by visual observation, it is possible to decide whether the sample contains the test substance or to measure the amount of the test substance.

In the immunochromatography method, in order to avoid a problem (false negative) in which antigens are not detected due to low sensitivity, a method of amplifying detection signal is implemented in some cases. As the signal amplification method, there is a method of using enzymes such as alkaline phosphotase or peroxidase as a label. Moreover, in some cases, antigens are detected by sensitizing labels selected from a group consisting of colloidal metal labels and metal sulfide labels with a silver ion-containing compound and a reductant for the silver ions (silver amplification).

JP2009-216695A discloses an immunochromatography method in which a washing solution is developed such that an angle of 45° to 170° is formed between the developing direction of a test substance and the developing direction of the washing solution. The document discloses that silver amplification may be performed, and bovine serum albumin (BSA)-containing phosphate buffered saline (PBS) is used as the washing solution.

Meanwhile, JP1994-167499A (JP-H06-167499A) discloses a solid-phase immunoassay in which a solution containing guanidine hydrochloride, thiocyanate, or urea is used to remove or wash antigens to be measured, antibodies to be measured, and/or unreacted labels. JP1995-159406A (JP-H07-159406A) discloses a method of washing labeling substances, which have been non-specifically adsorbed onto a reaction container and carriers for making immune components to be in a solid-phase, with a washing solution containing a sugar-based nonionic surfactant and chaotropic ions. JP1991-2662A (JP-H03-2662A) discloses an immunoassay system in which a chaotropic solution is used as a washing solution. JP1999-146783A (JP-H11-146783A) discloses a ribonucleic acid extraction method in which foreign substances which are not nucleic acids and have been non-specifically adsorbed onto carriers are washed with a solution containing a chaotropic substance.

SUMMARY OF THE INVENTION

In the immunochromatography method, if amplification is performed to increase sensitivity, a trace of labeling substances such as fine labeling particles present at the site on insoluble carriers, onto which binding substances such as antibodies binding specifically to the test substance have not been immobilized, are also amplified, and accordingly, a background level increases. Therefore, by performing washing or the like on the trace of labeling substances present on the insoluble carriers to reduce the amount thereof, the background level can be reduced, and at the same time, the sensitivity can be improved. On the contrary, if the washing is performed to improve the sensitivity, and thus the background level is reduced, the trace of the labeling substances having been non-specifically adsorbed onto the binding substances immobilized onto the insoluble carriers are amplified, and this results in false positives in many cases. The false positive results are obtained since a line (false-positive), which has not been observed due to being buried under the background level, is noticed when there is the reduction in the background level. Moreover, depending on the composition of the washing solution, the antibodies having been immobilized onto the insoluble carriers are also washed off in some cases. In these cases, high sensitivity cannot be obtained.

In addition, it was found that when the washing is performed using the chaotropic reagent disclosed in JP1994-167499A (JP-H06-167499A), JP1995-159406A (JP-H07-159406A), JP1991-2662A (JP-H03-2662A), and JP1999-146783A (JP-H11-146783A), and then the amplification is performed to increase sensitivity, if a large amount of the chaotropic reagent remains at the time of the amplification reaction, the background level of the site on the insoluble carriers to which the binding substances have not been immobilized increases, hence high sensitivity cannot be obtained. Therefore, the present invention aims to provide a chromatography method and a chromatography kit which make it possible to realize high sensitivity and a high S/N ratio (a ratio of signal to noise) while suppressing background noise made by non-specific adsorption.

In order to achieve the above object, the present inventors have conducted thorough examinations. As a result, they found that by chronologically performing steps of causing a complex composed of a test substance and a labeling substance to be trapped in a reaction site on an insoluble carrier, washing the insoluble carrier with a cleaning solution containing at least one of the potassium iodide, urea, and guanidine, washing off the washing solution remaining in the insoluble carrier from the insoluble carrier, and amplifying the labeling substance, it is possible to realize high sensitivity and a high S/N ration while suppressing background noise. The present invention has been completed based on the above findings.

That is, according to the present invention, there is provided a chromatography method including:

(a) developing a complex of a test substance and a labeling substance modified with a first binding substance bindable to the test substance, onto an insoluble carrier, (b) causing the complex to be trapped in a reaction site on the insoluble carrier which contains a second binding substance bindable to the test substance or a substance exhibiting binding properties to the first binding substance, (c) washing the insoluble carrier with a washing solution containing at least one of the potassium iodide, urea, and guanidine after the step (b), (d) washing off the washing solution remaining in the insoluble carrier from the insoluble carrier, and (e) amplifying the labeling substance of the complex trapped in the reaction site.

In the step (d), it is preferable to use a first amplification solution containing a reductant capable of reducing silver ion to wash off the washing solution from the insoluble carrier. In the step (e), it is preferable to use a second amplification solution containing a silver ion-containing compound to amplify the labeling substance of the complex.

The concentration of at least one of the potassium iodide, urea, and guanidine contained in the washing solution of the step (c) is preferably 25 mmol/L to 1,000 mmol/L.

In the step (c), the amount of at least one of the potassium iodide, urea, and guanidine applied to the insoluble carrier is preferably 0.8 μg/mm² to 300 μg/mm².

It is preferable to make the washing solution of the step (c) to flow, forming an angle of 45° to 135° with respect to the developing direction of the test substance.

It is preferable to make the first amplification solution to flow, forming an angle of 45° to 135° with respect to the developing direction of the test substance.

The labeling substance is preferably metal colloid.

The metal of the metal colloid is preferably gold, silver, platinum, or palladium.

The reductant capable of reducing silver ion is preferably $Fe^{2+}$.

It is preferable for the washing solution of the step (c) to contain at least one of the potassium iodide, urea, and guanidine and have pH of 5 to 8.

Moreover, according to the present invention, there is provided a chromatography kit including:

(A) a labeling substance modified with a first binding substance bindable to a test sub stance, (B) an insoluble carrier having a reaction site which contains a second binding substance bindable to the test substance or a substance exhibiting binding properties to the first binding substance, (C) a washing solution containing at least one or more among potassium iodide, urea, and guanidine, (D) a first amplification solution containing a reductant capable of reducing silver ion, and (E) a second amplification solution containing a silver ion-containing compound.

The concentration of at least one of the potassium iodide, urea, and guanidine that is contained in (C) the washing solution is preferably 25 mmol/L to 1,000 mmol/L.

The labeling substance is preferably metal colloid.

The metal of the metal colloid is preferably gold, silver, platinum, or palladium.

The reductant capable of reducing silver ion is preferably $Fe^{2+}$.

It is preferable for (C) the washing solution to contain only one of the potassium iodide, urea, and guanidine and to have pH of 5 to 8.

According to the chromatography method and chromatography kit of the present invention, it is possible to realize high sensitivity and a high S/N ratio while suppressing background noise.

DESCRIPTION OF THE PREFERRED EMBODIMENTS

Figure 1:
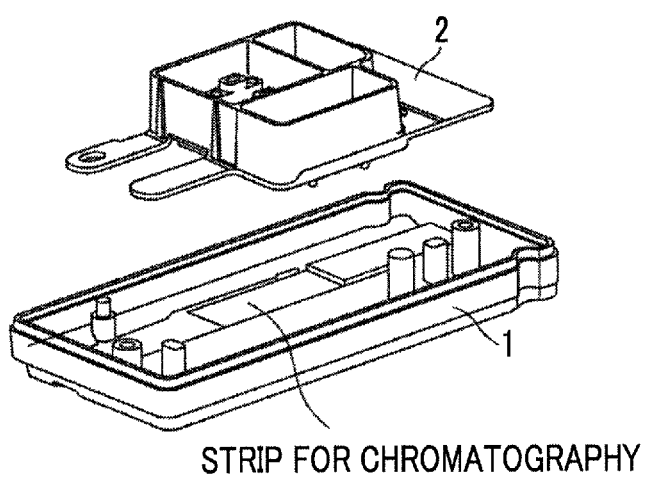
FIG. 1 is a schematic view of an exploded chromatography kit that can be used for the assay method of the present invention.

Hereinafter, the present invention will be described in more detail.

The present invention relates to a chromatography method including (a) a step of developing a complex of a test substance and a labeling substance modified with a first binding substance bindable to the test substance, onto an insoluble carrier, (b) a step of causing the complex of the test substance and the labeling substance, to be trapped in a reaction site on the insoluble carrier which contains a second binding substance bindable to the test substance or a substance exhibiting binding properties to the first binding substance bindable to the test substance, (c) a step of washing the insoluble carrier with a washing solution containing at least one of the potassium iodide, urea, and guanidine after the step (b), (d) a step of washing off the washing solution of the step (c) remaining in the insoluble carrier from the insoluble carrier, and (e) a step of amplifying the labeling substance of the complex trapped in the reaction site.

According to the present invention, before the labeling substance is amplified, the insoluble carrier is washed with the washing solution containing at least one of the potassium iodide, urea, and guanidine. The potassium iodide, urea, and guanidine increase entropy of water by means of diminishing interaction between water molecules and make the structure of water unstable. In the present invention, the insoluble carrier is washed with the washing solution containing at least one of the potassium iodode, urea, and guanidine, and then the signal is amplified to increase sensitivity. However, if the amplification is performed in a state where the potassium iodide, urea, or guanidine is in the reaction site, this leads to a problem in which the background level increases. In the present invention, after the insoluble carrier is washed with the washing solution containing at least one of the potassium iodide, urea, and guanidine, the washing solution remaining in the insoluble carrier is washed off from the insoluble carrier, and then the labeling substance is amplified. According to a preferable embodiment of the present invention, the potassium iodide, urea, or guanidine contained in the washing solution can be washed off by the first amplification solution containing the reductant capable of reducing silver ion, and silver amplification can be performed using the second amplification solution after the reaction site is filled with the reductant contained in the first amplification solution. According to the present invention, by the above operation, it is possible to significantly suppress the background level and to realize an extremely high S/N ratio.

1. Step of Washing Insoluble Carrier with Washing Solution Containing at Least One of the Potassium Iodide, Urea, and Guanidine The washing solution used in the present invention is a solution that contains at least one of the potassium iodide, urea, and guanidine. The urea can be used in the form of a hydrochloride of urea. Moreover, the guanidine is preferably used in the form of a salt such as guanidine hydrochloride, guanidine nitrate, guanidine carbonate, or guanidine phosphate, and particularly preferably used in the form of guanidine hydrochloride.

The concentration of at least one of the potassium iodide, urea, and guanidine in the washing solution is not particularly limited as long as the solution can exert a washing effect. However, the concentration is preferably 15 mmol/L to 1,500 mmol/L, and more preferably 25 mmol/L to 1,000 mmol/L. The pH of the washing solution is not particularly limited as long as the solution can exert a washing effect. However, the pH is preferably 5 to 8, and more preferably 6.5 to 7.5.

It is particularly preferable for the washing solution to be an aqueous solution that contains at least one of the potassium iodide, urea, and guanidine and has pH of 5 to 8. The aqueous solution containing at least one of the potassium iodide, urea, and guanidine refers to an aqueous solution that does not contain a substance other than potassium iodide, urea, guanidine, water, an acid or a base formed as a salt, and an acid or a base (for example, NaOH) that may be used in some cases to adjust pH.

The amount of at least one of the potassium iodide, urea, and guanidine applied to the insoluble carrier is not particularly limited as long as the washing solution can exert a washing effect. However, the amount is preferably 0.8 $\mu g/mm^2$ to 300 $\mu g/mm^2$, more preferably 1.5 $\mu g/mm^2$ to 200 $\mu g/mm^2$, and even more preferably 2.0 $\mu g/mm^2$ to 150 $\mu g/mm^2$.

The washing solution is developed while washing the non-specifically remaining labeling substance. Accordingly, the washing solution is developed while being mixed with the labeling substance. However, as the washing solution is not yet developed, it is preferable to use a solution free of the labeling substance so as to enhance the washing effect.

After the solution containing a complex of the test substance and the labeling substance modified with the first binding substance bindable to the test substance, is developed (hereinafter, described as "the solution containing the test substance is developed" or "the test substance is developed"), the washing solution is added to the insoluble carrier to wash the labeling substance that remains in the insoluble carrier without binding to the test substance by a specific binding reaction. As the method of sending the washing solution, the following may be used. The methods include a method in which a solution containing the test substance is developed and then directly added dropwise to a portion to which the solution is supposed to be added; a method in which an insoluble carrier for sending a solution (washing solution addition pad) and an insoluble carrier for absorption (water absorbing pad) for sending the washing solution are attached beforehand to the insoluble carrier, and then the washing solution is added to the insoluble carrier for sending a solution and sent toward the insoluble carrier for absorption; and a method in which a washing solution addition site is provided beforehand to the insoluble carrier, the solution containing the test substance is developed, and then the washing solution is added to the washing solution addition site. Alternatively, after the solution containing the test substance is developed onto the insoluble carrier, the insoluble carrier for sending a solution or the insoluble carrier for absorption for sending the washing solution may be attached to the insoluble carrier.

The insoluble carrier for sending a solution is not particularly limited as long as the washing solution can be added thereto, and a glass fiber pad, a cellulose membrane, nitrocellulose membrane, and the like can be used. The insoluble carrier for absorption is not particularly limited as long as it is made of a material that can absorb water, and cellulose, nitrocellulose, glass fiber, a mixture of these, and the like can be used.

The immunoassay represented by immunochromatography needs to have high sensitivity and high reproducibility, to have high accuracy when performing assay, and to have excellent storability. However, for making diagnosis in medical practice, the immunoassay needs to be convenient to such a degree where each medical office can perform assay, and the assay can be completed in a short time where the assay result can be confirmed on the spot. In the present invention, in order to perform the assay in a short time, it is preferable to make the washing solution to flow, forming an angle of 45° to 135° with respect to the developing direction of the test substance. In other words, in the present invention, it is preferably to make the washing solution to flow, forming an angle of 45° to 135° with respect to a longitudinal direction of the insoluble carrier. In the present invention, a direction in which the test substance is developed on the insoluble carrier is defined as the longitudinal direction. In the present invention, in order to shorten the time taken for the washing step using the washing solution and to obtain an excellent S/N ratio by means of enhancing the washing efficiency, the washing solution is more preferably made to flow, forming an angle of 60° to 120° C. with respect to the developing direction of the test substance, even more preferably made to flow, forming an angle of 75° to 110° with respect to the developing direction of the test substance, and most preferably made to flow, forming an angle of 90° with respect to the developing direction of the test substance.

2. Step of Washing Off Washing Solution Remaining in Insoluble Carrier from Insoluble Carrier In the present invention, a step of washing off the washing solution remaining in the insoluble carrier from the insoluble carrier is performed, and then the labeling substance is amplified.

The solution used for washing off the washing solution remaining in the insoluble carrier from the insoluble carrier is not particularly limited as long as the effects of the present invention are obtained. However, it is preferable to use a first amplification solution (which will be described in detail below in the present specification) containing a reductant capable of reducing silver ion. If such a solution is used, the washing solution remaining in the insoluble carrier can be washed off from the insoluble carrier.

3. Amplification of Labeling Substance

The labeling substance can be amplified using an amplification solution containing an amplification reagent. The amplification reagent generates a colored compound or causes luminescence by performing catalytic reaction due to the action of the labeling substance or the test substance and thus can cause the amplification of the signal. The reagent can be used in the form of a solution containing the reagent, that is, in the form of an amplification solution. Examples thereof include a silver ion solution which causes precipitation of metallic silver on a metal label by means of physical development, a solution containing a phenylenediamine and a naphthol compound that turns into a dye due to the action of a peroxidase label and hydrogen peroxide, and the like.

Specifically, so-called developers as disclosed in general books in the field of photographical chemistry (for example, "Revised Version of Fundament of Photography Engineering-Silver Halide Photography" (complied by The Society of Photography and Imaging of Japan, CORONA PUBLISHING CO., LTD.), "Chemistry of Photography" (Akira Sasai, Shashinkogyo Co., Ltd.), and "The Newest Prescription Handbook" (Shinichi Kikuchi et al., Amiko Publishing Co., Ltd.)) can be used as the amplification solution. The amplification solution can be used without particular limitation, as long as it is a so-called physical developer containing silver ions that are mainly reduced to become metal colloid to be a core of development.

In the present invention, two kinds of amplification reagents can be used. Among the two kinds of amplification reagents used for amplifying the signal of the labeling substance trapped in the reaction site on the insoluble carrier, a first amplification reagent is preferably contained in a first amplification solution, a second amplification reagent is preferably contained in a second amplification solution, and the first and second amplification solutions are preferably sequentially added to the carrier to perform amplification. Specifically, as the amplification solution, for example, it is possible to use a combination of the first amplification solution containing a reductant capable of reducing silver ion and the second amplification solution containing a silver ion-containing compound.

4. First Amplification Solution

The first amplification solution contains a reductant capable of reducing silver ion. As the reductant capable of reducing silver ion, any of inorganic and organic materials or a mixture thereof can be used as long as the silver ions can be reduced to silver. Preferable examples of the inorganic reductant include reducible metal salts and reducible metal complex salts that can change a valency by metal ions such as $Fe^{2+}$, $V^{2+}$, and $Ti^{3+}$. When the inorganic reductant is used, oxidized ions need to be removed or rendered to be harmless by being formed into a complex or reduced. For example, when $Fe^{2+}$ is used as a reductant, a complex of $Fe^{3+}$ as an oxide can be formed using citric acid or ethylenediaminetetraacetic acid (EDTA) to render the oxidized ions harmless. In the present invention, it is preferable to use the aforementioned inorganic reductant. In a more preferable embodiment of the present invention, it is preferable to use a metal salt of $Fe^{2+}$ as the reductant.

Moreover, it is possible to use primary developing agents (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco dyes) used for wet-type silver halide photographic sensitive materials and other materials which are well known to those skilled in the related art, for example, the materials disclosed in U.S. Pat. No. 6,020,117B.

Ascorbic acid reductants are also preferable as the reductant. Useful ascorbic acid reductants include ascorbic acid and analogs, isomers, and derivatives thereof. Preferable examples thereof include D- or L-ascorbic acid and sugar derivatives thereof (for example, γ-lactoascorbic acid, glucoascorbic acid, fucoascorbic acid, glucoheptoascorbic acid, and maltoascorbic acid), sodium salts of ascorbic acid, potassium salts of ascorbic acid, isoascorbic acid (or L-erythroascorbic acid), salts thereof (for example, alkali metal salts, ammonium salts, or salts known in the related art), enediol-type ascorbic acid, enaminol-type ascorbic acid, thioenol-type ascorbic acid, and the like. Particularly, D-, L-, or D,L-ascorbic acid (and alkali metal salts thereof) or isoascorbic acid (or alkali metal salts thereof) are preferable, and sodium salts are preferable salts thereof. If necessary, a mixture of these reductants can be used.

In a preferable embodiment of the chromatography method of the present invention, in order to increase the amplification efficiency and shorten the time taken for the amplification step, the first amplification solution containing the reductant capable of reducing silver ion is preferably made to flow, forming an angle of 45° to 135° with respect to the developing direction of the test substance. In other words, in the present invention, the first amplification solution is preferably made to flow, forming an angle of 45° to 135° with respect to the longitudinal direction of the insoluble carrier, more preferably made to flow, forming an angle of 60° to 120° with respect to the developing direction of the test substance, even more preferably made to flow, forming an angle of 75° to 110° with respect to the developing direction of the test substance, and most preferably made to flow, forming an angle of 90° with respect to the developing direction of the test substance.

5. Second Amplification Solution

The second amplification solution contains a silver ion-containing compound. As the silver ion-containing compound, for example, organic silver salts, inorganic silver salts, or silver complexes can be used. It is preferable to use silver ion-containing compounds exhibiting high solubility in a solvent such as water. Examples of such compounds include silver nitrate, silver acetate, silver lactate, silver butyrate, silver thiosulfate, and the like. Among these, silver nitrate is particularly preferable. As the silver complexes, silver complexes coordinated to a ligand having water-soluble groups such as hydroxyl groups or sulfone groups are preferable, and examples thereof include hydroxythioether silver and the like.

The organic silver salts, inorganic silver salts, and silver complexes are preferably contained in the form of silver to the amplification solution, at a concentration of 0.001 mol/L to 5 mol/L, preferably at a concentration of 0.005 mol/L to 3 mol/L, and even more preferably at a concentration of 0.01 mol/L to 1 mol/L.

6. Other Auxiliary Agents of Amplification Solution

The amplification solution contains a buffer, a preservative, or, for example, an antioxidant, an organic stabilizer, or a speed regulator, as other auxiliary agents. As the buffer, for example, it is possible to use acetic acid, citric acid, sodium hydroxide, or salts of any of these, a buffer using tris (hydroxymethyl)aminomethane, and other buffers that are used in general chemical experiments. If these buffers are appropriately used, pH can be adjusted to the level optimal for the amplification solution. Moreover, as an antifog agent, alkylamine can be used as the auxiliary agent, and particularly, dodecyamine is preferable. Furthermore, in order to improve solubility of these auxiliary agents, a surfactant can be used, and particularly, $C_9H_{19}$—$C_6H_4$—O—$(CH_2CH_2O)_{50}H$ is preferable.

7. Method of Landing Second Amplification Solution and Method of Storing Amplification Solution As a method of landing the second amplification solution on the chromatography kit, a method is preferable in which the first amplification solution is provided to a reaction site in a pad for sending the reductant solution, and then the silver ion solution as the second amplification solution is made to land on an area including the reaction site from above the area such that the silver ion solution infiltrates the insoluble carrier in the thickness direction thereof.

As a method of storing the first and second amplification solutions in the chromatography kit, for example, there is a method of disposing pots, which contain a solution containing each of the amplification reagents, to the upper portion of the sites on which each of the amplification reagents will be landed. It is preferable that the reductant solution (the first amplification solution) be placed in the upper portion of the pad for sending the reductant solution, and a pot containing the silver ion solution (the second amplification solution) be placed at a portion right above the hole to be filled with the silver ion solution. If the amplification solutions are disposed as above, by pressing each pot, the solution can flow and land on a predetermined site.

8. Chromatography

The present invention is a chromatography method for amplifying detection signal. Generally, a chromatography method is a technique of specifically identifying and measuring a test substance in a convenient and rapid manner by the following technique. That is, a chromatography carrier (a portion of the insoluble carrier), which can have at least one reaction site which contains a binding substance (corresponding to the second binding substance bindable to the test substance or the substance exhibiting binding properties to the first binding substance which will be described below; specifically, an antibody, an antigen, and the like) that can bind to the test substance, is used as a stationary phase. On the chromatography carrier, a solution, which contains the labeling substance modified with the first binding substance that binds to the test substance, is made to move as a mobile layer and reaches the area having the reaction site while the test substance is binding specifically to the labeling substance. In the reaction site, the complex of the test substance and the labeling substance binds to the immobilized second binding substance or binds specifically to the substance exhibiting binding properties to the first binding substance. At this time, only when the test sample contains the test substance, the labeling substance is concentrated to the second binding substance or to the substance exhibiting binding properties to the first binding substance. The chromatography method is a technique that utilizes the above phenomenon and analyzes qualitatively and quantitatively whether the test sample contains the test substance, by means of visual observation or using appropriate instruments.

In the chromatography method of the present invention, after the complex of the test substance and the labeling substance binds to the immobilized second binding substance or binds specifically to the substance exhibiting binding properties to the first binding substance in the reaction site, the reaction site is washed with the washing solution, and then the signal is amplified using the amplification solution. As the amplification reagents used for amplifying the signal of the labeling substance, two kinds of amplification reagents, for example, the reductant capable of reducing silver ion and the silver-containing compound are preferably used, and the complex of the test substance and the labeling substance that has bound to the binding substance immobilized in the reaction site is used as a core for performing the amplification reaction. As a result, the signal can be amplified, and consequently, high sensitivity can be obtained. According to the present invention, high-sensitive chromatography can be performed rapidly.

9. Test Sample

The test sample that can be analyzed using the chromatography method and chromatography kit of the present invention is not particularly limited as long as it is a sample likely containing the test substance. Examples of the test sample include biological samples, particularly, body fluid (for example, blood, serum, plasma, spinal fluid, tear, sweat, urine, pus, nasal discharge, or sputum), excrement (for example, stool), organs, tissues, mucous membrane, and skin of animals (particularly, human beings), scrapings (swabs) considered to contain these, mouthwash, and animals and plants or dry preparation thereof. Examples of the test substance include natural substances, toxins, hormones, bioactive substances such as agrochemicals, environmental pollutants, virus, antigens, antibodies, and the like.

10. Pretreatment of Test Sample

In the chromatography method of the present invention, the test sample can be used as is. Alternatively, the test sample can be used in the form of an extract which is obtained by extracting the test sample by using an appropriate solvent for extraction, in the form of a diluted solution obtained by diluting the extract with an appropriate diluent, or in the form of a concentrate obtained by concentrating the extract by an appropriate method. As the solvent for extraction used in the present invention, it is possible to use solvents (for example, water, physiological saline, a buffer solution, and the like) that are used in general immunological analysis or to use water-miscible organic solvents that can directly cause an antigen-antibody reaction by being diluted with the aforementioned solvents.

11. Configuration

A strip for chromatography can be used by being incorporated into the chromatography kit which is for performing the chromatography method of the present invention. The strip for chromatography can be used without particular limitation as long as it can be used for the general chromatography method.

The strip for chromatography that can be used in the present invention has a labeling substance holding area and a reaction area extending from the upstream to the downstream in the developing direction of the test sample containing the test substance. For example, an embodiment is preferably used in which a sample addition pad, a labeling substance holding pad (for example, a metal colloid antibody holding pad) that has a labeling substance holding area, a binding substance-immobilized membrane (for example, a chromatography carrier having a reaction site) that is an insoluble carrier, and a water absorbing pad are disposed in this order on an adhesive sheet. The chromatography carrier as an insoluble carrier in which the binding substance has been immobilized has an area that includes at least one reaction site (test line) in which an antibody or an antigen binding specifically to the test substance has been immobilized. If desired, the chromatography carrier may further have an area that includes at least one control line in which a control antibody or a control antigen has been immobilized.

The labeling substance holding pad having the labeling substance holding area that can be used in the present invention can be prepared by preparing a suspension containing the labeling substance, coating an appropriate water absorbing pad (for example, a glass fiber pad) with the suspension, and then drying the pad.

11-1. Labeling Substance

As the labeling substance used in the present invention, it is preferable to use metal-containing labeling substances. The metal that can be preferably used in the present invention includes precious metals such as gold, silver, platinum, and palladium, iron, lead, copper, cadmium, bismuth, antimony, tin, and mercury. Among these, the precious metals such as gold, silver, platinum, and palladium can be even more preferably used. The metal-containing labeling substances that can be used in the present invention are preferably used in the form of a metal colloid label or a metal sulfide label. In the present invention, as the metal colloid label, platinum colloid, gold colloid, silver colloid, palladium colloid, iron colloid, aluminum hydroxide colloid, and the like can be preferably used. As the metal sulfide label, sulfides of iron, silver, lead, copper, cadmium, bismuth, antimony, tin, or mercury can be preferably used. In the present invention, platinum colloid, gold colloid, silver colloid, and palladium colloid can be even more preferably used, and gold colloid can be most preferably used. When gold colloid particles are used as the metal colloid label, commercially available products may be used. Alternatively, it is possible to prepare gold colloid by a common method, for example, the method of reducing chloroauric acid by using sodium citrate (Nature Physical Science, 241 (1973), 20, and the like).

The average particle size of the metal colloid is preferably about 1 nm to 500 nm, more preferably 3 nm to 100 nm, and particularly preferably 5 nm to 60 nm. The average particle size of the metal colloid used in the present invention can be measured by a commercially available particle size distribution analyzer and the like. As the particle size distribution analysis method, an optical microscopic method, a confocal laser microscopic method, an electron microscopic method, an atomic force microscopic method, a static light scattering method, a laser diffraction method, a dynamic light scattering method, a centrifugal precipitation method, an electric pulse measuring method, a chromatography method, an ultrasonic attenuation method, and the like are known, and devices corresponding to the principles of the respective methods are commercially available.

In view of the range of particle size and ease of measurement, a dynamic light scattering method can be preferably used in the present invention. Examples of commercially available analyzers utilizing dynamic light scattering include Nanotrac UPA (NIKKISO CO., LTD.), a dynamic light scattering-type particle size distribution analyzer LB-550 (HORIBA, LTD.), a concentrated system-particle size analyzer FPAR-1000 (OTSUKA ELECTRONICS CO., LTD.), and the like. In the present invention, a value of median diameter (d=50) measured at 25° C. can be taken as the average particle size.

According to the present invention, in chromatography that uses, as a labeling substance, the metal colloid label or the metal sulfide label, other metal alloy labels (hereinafter, referred to as "metallic labels" in some cases), or metal-containing polymer particle labels, it is preferable to amplify the signal of the metallic label. Specifically, after a complex of the test substance and the labeling substance which has been modified with the first binding substance bindable to the test substance is trapped in the reaction site, silver ions supplied from the silver-containing compound, such as inorganic silver salts or organic silver salts, are brought into contact with the reductant capable of reducing silver ion. As a result, silver particles are generated due to silver ion reduction caused by the reductant, and the silver particles are deposited onto the metallic label by using the metallic label as a core. Accordingly, the metallic label is amplified, whereby the test substance can be analyzed with high sensitivity. Therefore, in the chromatography method of the present invention, the conventionally known chromatography method can be used as is, except that the silver particles generated by silver ion reduction caused by the reductant are deposited onto the labeling substance, and the signal amplified in this manner is analyzed.

11-2. Binding Substance

In the present invention, the labeling substance has been modified with the first binding substance bindable to the test substance. The first binding substance is not particularly limited as long as it is a compound having affinity with the test substance, such as an antibody binding specifically to the test substance formed of an antigen, an antigen binding specifically to the test substance formed of an antibody, proteins, and an aptamer binding to the test substance formed of a low-molecular weight compound or the like.

In the chromatography kit of the present invention, the second binding substance bindable to the test substance or the binding substance exhibiting binding properties to the first binding substance is positioned at the reaction site on the insoluble carrier. The second binding substance bindable to the test substance includes, for example, an antibody binding specifically to the test substance formed of an antigen, an antigen binding specifically to the test substance formed of an antibody, proteins, an aptamer binding to the test substance formed of a low-molecular weight compound or the like, and is not particularly limited as long as it is a compound having affinity with the test substance. Moreover, the second binding substance and the first binding substance may be the same as or different from each other. The substance exhibiting binding properties to the first binding substance may be the test substance or a compound having a site recognized by the first binding substance. The substance exhibiting binding properties to the first test substance includes, for example, compounds that may bond the derivatives of the test substance to a protein (for example, BSA) and the like.

It is preferable for the first and second binding substances to be antibodies. Alternatively, it is preferable for either the first binding substance or the second binding substance to be an antibody. Moreover, it is acceptable to use an embodiment in which the first binding substance is an antibody and the second binding substance is an antibody binding to the first binding substance.

In the chromatography method of the present invention, the antibody exhibiting specificity with respect to the test substance is not particularly limited. For example, it is possible to use antiserum prepared from the serum of an animal immunized with the test substance, an immunoglobulin fraction purified from antiserum, monoclonal antibodies obtained by cell fusion using splenocytes of an animal immunized with the test substance, or fragments thereof (for example, F(ab')2, Fab, Fab', or Fv). These antibodies can be prepared by common methods.

In the present invention, for example, when the metal colloid is bonded to a specific binding substance, the labeling substance can be modified with the first binding substance, according to the conventionally known method (for example, The Journal of Histochemistry and Cytochemistry, 30, 7 (1982), 691-696) described below. Specifically, for example, the metal colloid is mixed with the specific binding substance (for example, an antibody) for 5 minutes or a longer at room temperature in an appropriate buffer solution. After the reaction, the precipitate obtained by centrifugation is dispersed in a solution containing a dispersant such as polyethylene glycol, whereby a target metal colloid-labeled specific binding substance can be obtained.

11-3. Insoluble Carrier

As the insoluble carrier that can be used in the present invention, porous carriers are preferable. Particularly, a nitrocellulose membrane, a cellulose membrane, an acetyl cellulose membrane, a polysulfone membrane, a polyethersulfone membrane, a nylon membrane, glass fiber, non-woven cloth, cloth, a thread, and the like are preferable.

In the present invention, the insoluble carrier for chromatography has a reaction site in which the second binding substance bindable to the test substance or the substance exhibiting binding properties to the first binding substance has been immobilized. The second binding substance bindable to the test substance or the substance exhibiting binding properties to the first binding substance may be directly immobilized onto a portion of the insoluble carrier by means of physical or chemical bonding so as to form the reaction site. Alternatively, the second binding substance or the substance exhibiting binding properties to the first binding substance may be physically or chemically bonded to fine particles such as latex particles, and the fine particles may be immobilized by being trapped in a portion of the insoluble carrier so as to form the reaction site. Moreover, it is preferable to use the insoluble carrier after it undergoes immobilization of the second binding substance or the substance exhibiting binding properties to the first binding substance and then subjected to non-specific adsorption preventing treatment using an inactivating protein or the like. It is also possible to preferably use an embodiment in which the insoluble carrier of the present invention has plural reaction sites. Furthermore, if desired, the insoluble carrier may have at least one control line in which the aforementioned control antibody or antigen has been immobilized.

11-4. Labeling Substance Holding Pad

In the present invention, it is preferable for the labeling substance holding pad having the labeling substance holding area to be used in an embodiment in which a gold colloid holding pad is incorporated into the insoluble carrier (insoluble carrier for chromatography). As the material of the labeling substance holding pad, for example, cellulose filter paper, glass fiber, non-woven cloth, and the like can be preferably used. By impregnating the pad with the labeling substance prepared as above in a certain amount and drying the pad, the labeling substance holding area can be formed.

11-5. Sample Addition Pad

It is preferable for the insoluble carrier (insoluble carrier for chromatography) used in the present invention to be used in a state where a sample addition pad is incorporated into the carrier. It is preferable for the sample addition pad to be used in an embodiment in which it functions not only to receive the test substance-containing sample added thereto but also to filter out insoluble particles in the sample. Examples of the material of the sample addition pad include materials having uniformity such as cellulose filter paper, glass fiber, polyurethane, polyacetate, cellulose acetate, nylon, and cotton cloth. Moreover, in order to prevent the test substance in the sample from being non-specifically adsorbed onto the material of the sample addition pad at the time of analysis and thus deteriorating the accuracy of the analysis, the material composing the sample addition portion can be used after being subjected to non-specific adsorption preventing treatment. In the present invention, the sample addition pad may also function as the labeling substance holding pad having the labeling substance holding area described in the section 11-4.

11-6. Water Absorbing Pad

In the present invention, a water absorbing pad can be used by being preferably incorporated into the insoluble carrier (strip for chromatography). The water absorbing pad is a site that physically absorbs the sample added thereto by chromatographic movement and absorbs and removes an unreacted labeling substance or the like that does not undergo insolubilization in the detection portion of the chromatography carrier. For the water absorbing pad, water absorbing materials such as cellulose filter paper, non-woven cloth, cloth, and cellulose acetate are used. The speed of chromatography, which is started after the chromatographic leading end of the added sample reaches the water absorbing pad, varies with the material, size, and the like of the water absorbing pad. Accordingly, by appropriately selecting the material, size, and the like, it is possible to set the speed suitable for measuring the test substance.

12. Method of Immunological Test

Hereinafter, regarding the chromatography method of the present invention, a sandwich method, which is a specific embodiment of the chromatography method, will be described.

The sandwich method is not particularly limited. However, for example, a test substance can be analyzed by the method according to the following procedure. First, a first binding substance (for example, a first antibody) and a second binding substance (for example, a second antibody) specific for a test substance (for example, an antigen) are prepared in advance by the method described above. Moreover, a labeling substance is modified in advance with the first binding substance. In addition, the second binding substance is immobilized onto an appropriate chromatography carrier (insoluble carrier) (for example, a nitrocellulose membrane, a glass fiber membrane, a nylon membrane, or a cellulose membrane) to form a reaction site and is brought into contact with a test sample (or an extract thereof) likely containing the test substance. At this time, if the test sample contains the test substance, the second binding substance binds to the test substance (for example, an antigen-antibody reaction occurring between the test substance and the second antibody). Further, while the test substance is binding to the second binding substance, or after the test substance binds to the second test substance, an excess amount of a labeling substance modified with the first binding substance is brought into contact with the test sample. At this time, if the test sample contains the test substance, a complex consisting of the immobilized second binding substance, the test substance, and the labeling substance modified with the first binding substance is formed.

In the sandwich method, after the reaction between the immobilized second binding substance and the test substance and the reaction between the test substance and the first binding substance having modified the labeling substance end, the labeling substance not forming an immunocomplex is removed. Subsequently, for example, the reaction site of the insoluble carrier is observed as is so as to detect or quantitate the labeling substance. In this manner, it is possible to determine whether or not the test sample contains the test substance or to measure the amount of the test substance. In the present invention, for example, by supplying the reductant capable of reducing silver ion and the silver ion-containing compound, the signal from the labeling substance which has formed the aforementioned complex is amplified and detected.

13. Chromatography Kit

The chromatography method of the present invention can be performed using a chromatography kit including a labeling substance modified with a first binding substance bindable to a test substance and an insoluble carrier which contains a second binding substance bindable to the test substance or a substance exhibiting binding properties to the first binding substance bindable to the test substance. In this case, in the chromatography kit, the labeling substance modified with the first binding substance bindable to the test substance may be disposed in advance on the insoluble carrier. Alternatively, in the chromatography kit, the labeling substance modified with the first binding substance bindable to the test substance may be prepared separately from the insoluble carrier. In this case, the test substance can be measured by a method of mixing the labeling substance prepared separately from the insoluble carrier with the test substance and then developing the mixture on the insoluble carrier, and the like. The chromatography kit of the present invention contains a washing solution and an amplification solution. Preferably, the kit can contain an amplification solution containing a silver-containing compound and a reductant capable of reducing silver ion. For the examples of the respective materials constituting the chromatography kit and preferable range thereof, the examples and range described in the section relating to the chromatography method or the like can be preferably used.

Particularly, according to the present invention, there is provided a chromatography kit including:

(A) a labeling substance modified with a first binding substance bindable to a test sub stance, (B) an insoluble carrier having a reaction site which contains a second binding substance bindable to the test substance or a substance exhibiting binding properties to the first binding substance bindable to the test substance, (C) a washing solution containing at least one of the potassium iodide, urea, and guanidine, (D) a first amplification solution containing a reductant capable of reducing silver ion, and (E) a second amplification solution containing a silver ion-containing compound.

The labeling substance modified with the first binding substance bindable to the test substance may be disposed on the insoluble carrier or may be prepared separately from the insoluble carrier.

Hereinafter, the present invention will be described in more detail by examples, but the present invention is not limited to the examples.

EXAMPLES (1) Preparation of Chromatography Kit for Detecting Influenza Virus Antigen (1-1) Preparation of Anti-Influenza A Antibody-Modified Gold Colloid (1-1-1) Preparation of F(ab')$_2$ Fragment of Anti-Influenza A Virus Antibody By using an anti-influenza A virus antibody (product number 7307, manufactured by Medix Biochemica) and ImmunoPureIgG1 Fab and F(ab')$_2$ Preparation Kit (product number 44880, manufactured by Thermo Fisher Scientific, Inc.), F(ab')$_2$ fragments of the anti-influenza A virus antibody were prepared.

(1-1-2) Preparation of Gold Colloid Modified with Anti-Influenza A Antibody Fragment 1 mL of 50 mmol/L KH$_2$PO$_4$ buffer (pH 7.5) was added to 9 mL of a solution of gold colloid having a diameter of 50 nm (EM. GC50, manufactured by BBI Solutions) to adjust pH of the gold colloid solution. Subsequently, 1 mL of a 160 μg/mL solution containing the F(ab')$_2$ fragments of anti-influenza A virus antibody that was prepared in the section (1-1-1) was added to the above solution, followed by stirring. The solution was allowed to stand still for 10 minutes, and then 550 μL of an aqueous solution containing 1% by mass polyethylene glycol (PEG, molecular weight of 20,000, product number 168-11285, manufactured by Wako Pure Chemical Industries, Ltd.) was added thereto, followed by stirring. Thereafter, 1.1 mL of an aqueous solution containing 10% by mass bovine serum albumin (BSA Fraction V, product number A-7906, manufactured by Sigma-Aldrich Co, LLC.) was added thereto, followed by stirring. This solution was subjected to centrifugation for 30 minutes by using a centrifuge (Himac CF16RX, manufactured by Hitachi, Ltd.) under the condition of 8,000×g at 4° C. The supernatant was then removed except for about 1 mL of the solution, and the gold colloid was redispersed by an ultrasonic washing machine. The gold colloid having undergone redispersion was added to 20 mL of a gold colloid storage solution (20 mmol/L Tris-HCl buffer (pH 8.2), 0.05% by mass PEG (molecular weight 20,000), 150 mmol/L NaCl, 1% by mass BSA) and dispersed, followed by centrifugation again at 8,000×g and 4° C. for 30 minutes. Thereafter, the supernatant was removed except for about 1 mL of the solution, and the gold colloid was redipersed using an ultrasonic washing machine, thereby obtaining a gold colloid solution (diameter 50 nm) modified with anti-influenza A antibody fragments.

(1-2) Preparation of Pad for Holding Gold Colloid Modified with Anti-Influenza A Antibody Fragments The gold colloid modified with anti-influenza A antibody fragments that was prepared in the section (1-1-2) was diluted with a gold colloid coating solution (20 mmol/L Tris-HCl buffer (pH 8.2), 0.05% by mass PEG (molecular weight 20,000), 5% by mass sucrose) and water such that Absorbance of 520 nm became 0.04. A glass fiber pad (Glass Fiber Conjugate Pad, manufactured by Millipore Corporation) cut in 8 mm×150 mm was evenly coated with 0.8 mL of the above solution, dried for 12 hours under reduced pressure, and then cut in 8 mm×5 mm, thereby obtaining gold colloid antibody holding pads (labeling substance holding pads). The portion holding the gold colloid antibody corresponds to the labeling substance holding area.

(1-3) Preparation of Antibody-Immobilized Membrane (Insoluble Carrier for Chromatography)

Antibodies were immobilized onto a nitrocellulose membrane (lined with plastic, HiFlow Plus HF180, manufactured by Millipore Corporation) cut in 25 mm×200 mm by the following method, thereby preparing an antibody-immobilized membrane. The long side of the membrane was taken as the lower side, and a position 7 mm distant from the lower side was coated with a solution (containing sucrose and BSA) of anti-influenza A monoclonal antibodies for immobilization (Anti-Influenza A SPTN-5 7307, manufactured by Medix Biochemica) having a concentration of 1.5 mg/mL, in a line shape having a width of about 0.7 mm by using an injector-type coating machine (manufactured by BIODOT INC), thereby forming a reaction site. This line is called a test line. Similarly, a position 13 mm distant from the lower side was coated with a solution of anti-mouse IgG antibodies (anti-mouse IgG (H+L), rabbit F(ab')$_2$, product number 566-70621, manufactured by Wako Pure Chemical Industries, Ltd.) as a control having a concentration of 0.5 mg/mL in a line shape. This line is called a control line. The coated membrane was dried for 12 hours at room temperature, and then dried 2 days at 50° C. by being supplemented with a desiccant.

(1-4) Preparation of Chromatography Strip

The antibody-immobilized membrane prepared in the section (1-3) was bonded to a back adhesive sheet (ARcare 9020, manufactured by Nippn Techno Cluster, Inc.). At this time, in the long side of the membrane, the side of the test line was taken as the lower side. The plural gold colloid antibody holding pads prepared in the section (1-2) were stuck by overlapping in parallel so as to overlap approximately 2 mm to the lower side of the antibody-immobilized membrane. Moreover, sample addition pads (glass fiber pads cut in 18 mm×250 mm (Glass Fiber Conjugate Pad, manufactured by Millipore Corporation)) were stuck by overlapping so as to overlap approximately 4 mm to the lower side of the gold colloid antibody holding pads. In addition, water absorbing pads (cellulose/glass membranes (CF6, manufactured by Whatman plc) cut in 80 mm×250 mm) were stuck by overlapping so as to overlap approximately 5 mm to the upper side of the antibody-immobilized membrane. The obtained sheet of chromatography strip was cut so as to separate the adjacent gold colloid antibody holding pads from each other, thereby obtaining a chromatography strip having the width of 7 mm.

(1-5) Preparation of Washing Solution 1

KI (manufactured by Wako Pure Chemical Industries, Ltd.) was dissolved in ultrapure water to prepare a 200 mmol/L KI solution (adjusted to pH 7 by NaOH), thereby obtaining a washing solution 1.

(1-6) Preparation of Silver Amplification Solution (1-6-1) Preparation of Reductant Solution (First Amplification Solution)

23.6 mL of a 1 mol/L aqueous iron nitrate solution, which was prepared by dissolving iron(III) nitrate nonahydrate (095-00995, manufactured by Wako Pure Chemical Industries, Ltd.) in water, and 13.1 g of citric acid (038-06925, manufactured by Wako Pure Chemical Industries, Ltd.) were dissolved in 290 g of water. After the above components thoroughly dissolved, 36 ml of nitric acid (10% by weight) was added thereto by being stirred with a stirrer, and then 60.8 g of ammonium iron(II) sulfate hexahydrate (091-00855, Wako Pure Chemical Industries, Ltd.) was added thereto, thereby obtaining a reductant solution.

(1-6-2) Preparation of Silver Ion Solution (Second Amplification Solution)

8 mL of silver nitrate solution (containing 10 g of silver nitrate) and 24 mL of a 1 mol/L aqueous iron nitrate solution were added to 66 g of water. This solution was mixed with a solution which was obtained by dissolving in advance 5.9 mL of nitric acid (10% by weight), 0.1 g of dodecylamine (123-00246, manufactured by Wako Pure Chemical Industries, Ltd.), and 0.1 g of a surfactant $C_{12}H_{25}$—$C_6H_4$—O—($CH_2CH_2O)_{50}H$ in 47.6 g of water, thereby obtaining a silver ion solution.

(1-7) Preparation of Test Sample

A solution obtained by diluting a simulated influenza A-positive specimen (BD Flu Examan control A+B− (manufactured by Becton, Dickson and Company.)) with a tris buffer (5% by mass, containing Tween) was taken as a antigen-containing test sample. Moreover, a tris buffer (5% by mass, containing Tween) was taken as an antigen-free test sample.

(1-8) Device for Assay

Figure 2:
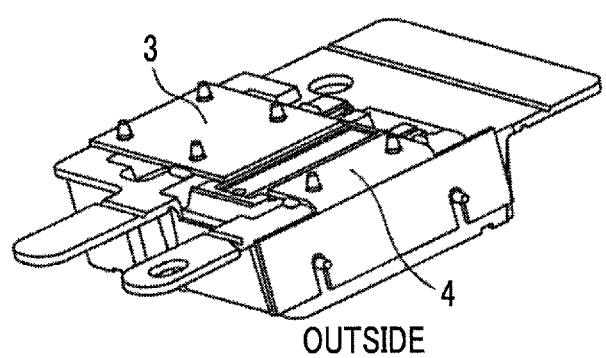
FIG. 2 is a view showing the front and back of a second device part.
Figure 2:
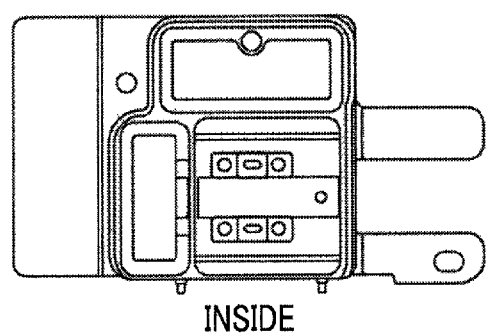
Figure 3A:
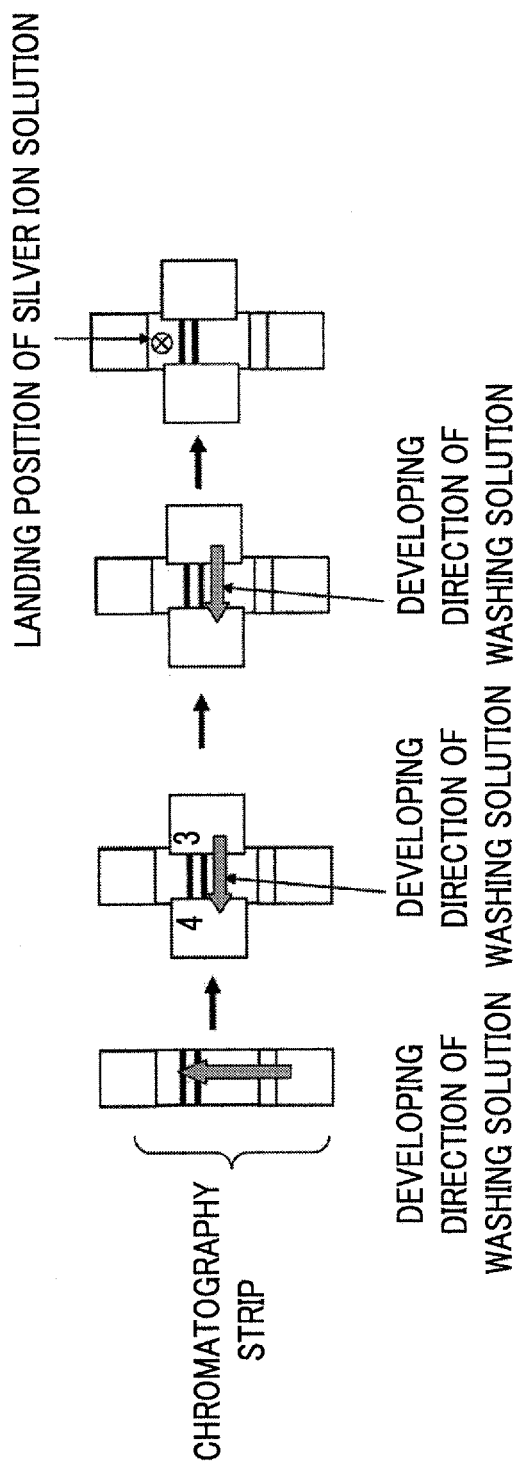
FIGS. 3A and 3B are schematic plan views showing a sequence of the assay method of the present invention.
Figure 3B:
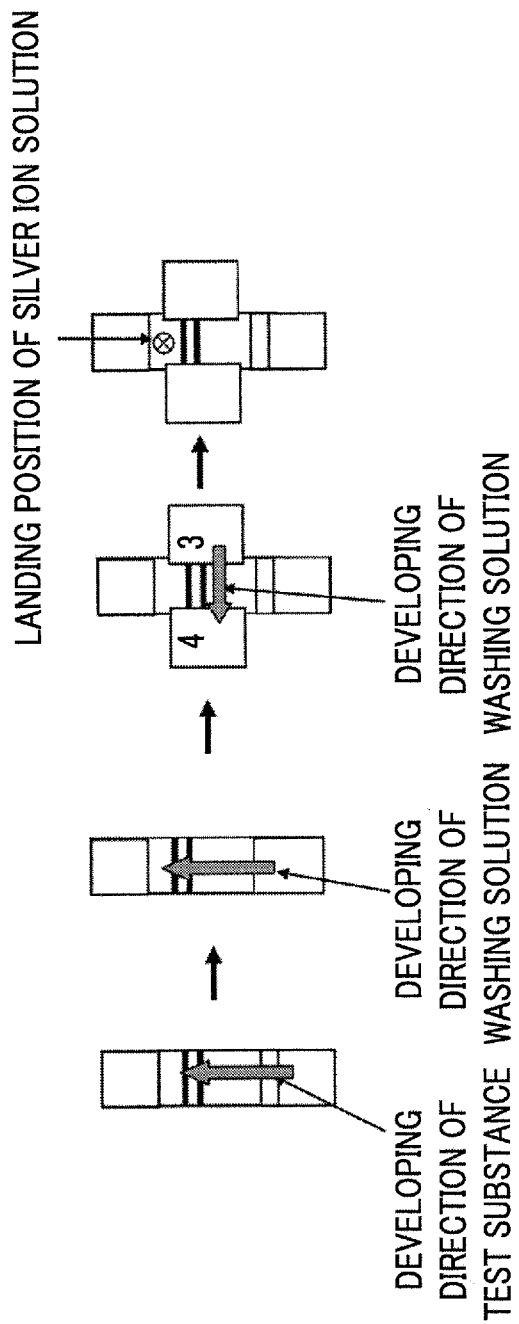

As shown in FIG. 1, the chromatography strip was loaded on a first device part 1 (made of polypropylene by means of injection molding) show in FIG. 1. Thereafter, as shown in FIG. 2, a second device part 2 (made of polypropylene by means of injection molding), on which glass fiber pads (Glass Fiber Conjugate Pad, manufactured by Millipore Corporation) had been loaded as a second insoluble carrier 3 and a third insoluble carrier 4, was loaded on the first device part. At this point in time, the chromatography strip had not yet come into contact with the members 2 to 4.

(2-1) Evaluation (2-1-1) Landing and Developing of Test Sample

The solution obtained by diluting a simulated influenza A-positive specimen (BD Flu Examan control A+B− (manufactured by Becton, Dickson and Company.)) with a tris buffer (5% by mass, containing Tween) or only a tris buffer (5% by mass, containing Tween) was landed in an amount of 140 µL on the sample addition pad of the chromatography kit for test that was prepared in the section (1-4) and allowed to stand still for 11 minutes.

(2-1-2) Washing

Example 1

After the test sample was developed for 11 minutes, the second device part 2 was pressed with a force of 50 N so as to bring the insoluble carriers 3 and 4 into contact with the chromatography strip. Immediately after the contact, 120 µL of the washing solution 1 (KI solution, 200 mmol/L, pH 7) prepared in the section (1-5) was added to a washing solution landing hole 5 of the second device part 2. In this manner, the washing solution was sent for 80 seconds from the direction forming 90° with respect to the longitudinal direction of the chromatography strip. By this step, the labels non-specifically adsorbed onto the site other than the reaction site on the chromatography strip were washed.

(2-1-3) Supply of Reductant Solution

After the washing was performed as described in the section (2-1-2), the second device part 2 was replaced with a new second device part 2. The new second device part 2 was pressed with a force of 50 N so as to bring the insoluble carriers 3 and 4 into contact with the chromatography strip. Immediately after the contact, 120 µL of the reductant solution prepared in the section (1-6-1) was added to the washing solution landing hole 5 of the second device part 2. In this manner, the reductant solution was sent for 80 seconds from the direction forming 90° with respect to the longitudinal direction of the chromatography strip. By this step, the washing solution component remaining on the chromatography strip was washed off, and the reductant solution for silver amplification was supplied.

(2-1-4) Silver Amplification

The silver ion solution prepared in the section (1-6-2) was added dropwise to the strip through a silver ion solution landing hole 6 placed in the second device part 2, and a silver amplification reaction was performed for 1 minute. After the amplification, the chromatography strip was detached and washed with water for 3 minutes.

(2-1-5) Calculation of Test Line Density

The chromatography strip washed with water was imaged with an image analyzer (LAS 4000, manufactured by GE Healthcare), and a test line ΔOD (difference in optical density (OD) between the test line and the antibody non-immobilized site of the chromatography strip) was calculated. ΔOD of the test line that was obtained when the sample contained the antigen was defined as signal (S), and ΔOD of the test line that was obtained when the sample did not contain the antigen was defined as false positive (N).

Example 2

A urea solution (200 mmol/L, pH 7) was prepared in the same manner as in Preparation of washing solution 1, except that KI was replaced with urea (manufactured by Wako Pure Chemical Industries, Ltd.). Moreover, the test line density was calculated in the same manner as in Example 1.

Example 3

A guanidine solution (200 mmol/L, pH 7) was prepared in the same manner as in Preparation of washing solution 1, except that KI was replaced with guanidine hydrochloride (manufactured by Wako Pure Chemical Industries, Ltd.), and pH thereof was adjusted using NaOH. Moreover, the test line density was calculated in the same manner as in Example 1.

Example 4

After the antigen-containing test sample was developed for 11 minutes, the sample addition pad and the labeling substance holding pad (gold colloid antibody holding pad) were removed. Thereafter, a glass fiber pad was newly bonded to the position of the sample addition pad, and 120 μL of a KI solution (200 mmol/L, pH 7) was added thereto. In this manner, the washing solution was sent for 300 seconds from the direction forming 0° with respect to the longitudinal direction of the chromatography strip. By this step, the labels non-specifically adsorbed onto the site other than the reaction site on the chromatography strip were washed. The operation following this step was performed in the same manner as in Example 1.

Comparative Example 1

Evaluation was performed without using the washing solution. That is, evaluation was performed in the same manner as in Example 1, except that the step of the section (2-1-2) was not conducted.

Comparative Example 2

Evaluation was performed in the same manner as in Example 1, except that the washing solution was replaced with ultrapure water (pH 7).

Comparative Example 3

Evaluation was performed in the same manner as in Example 1, except that the washing solution was replaced with a NaCl solution (200 mmol/L, pH 7).

Comparative Example 4

In the same manner as in Example 1, washing was performed by sending 120 μL of a KI solution (200 mmol/L, pH 7) from the direction forming 90° with respect to the longitudinal direction of the chromatography strip. Thereafter, the chromatography strip was dipped in a solution obtained by mixing the reductant solution with the silver ion solution at a ratio of 4:1 (volume ratio) to perform amplification for 1 minute. That is, in this example, the step of washing off the washing solution component by using the reductant solution was not performed.

(Results of Examples 1 to 4 and Comparative Examples 1 to 4)

Table 1 shows the results of Examples 1 to 4 and Comparative examples 1 to 4. From Table 1, it was understood that by washing the insoluble carrier with the washing solution prior to the silver amplification reaction so as to wash off the gold colloid non-specifically adsorbed onto the site other than the reaction site of the chromatography strip, the background level is reduced. However, when the insoluble carrier was washed with ultrapure water, the antibodies immobilized in the insoluble carrier are washed off, the signal (S) was not enhanced. On the contrary, when NaCl was added to the washing solution, though the signal (S) was enhanced since the antibodies are inhibited from being washed off, a rate of false positive (N) also increased. When KI, urea, or guanidine was added to the washing solution, the signal was enhanced, and the false positive was suppressed, and accordingly, a high S/N ratio equal to or higher than 15 could be obtained.

From the comparison between Examples 1 to 3 and Example 4, it was found that when the washing solution containing KI, urea, or guanidine is made to flow in the direction of 90°, the background level can be further reduced, and the signal (S) can be further enhanced, compared to the case where the washing solution is made to flow in the direction 0°. Moreover, when the washing solution was made to flow in the direction of 0°, it took 300 seconds for the washing solution to reach the downstream of the chromatography strip from the upstream thereof. On the contrary, when the washing solution was made to flow in the direction of 90°, the operation was completed in 80 seconds. Therefore, it was found that from the viewpoints of increasing sensitivity and shortening the time taken for the operation, it is preferable for the washing solution to flow in the direction of 90°.

However, KI, urea, or guanidine causes increase in the background level by the silver amplification reaction. Accordingly, when the insoluble carrier was washed with the washing solution containing these reagents, and then the silver amplification reaction was performed in a state where the reagents remained in the carrier, the background level was not reduced, and the signal (S) was not enhanced. (Comparative example 4)

The above results show that the most preferable embodiment may be a method of sending KI, urea, or guanidine in the direction of 90° with respect to the chromatography strip and then causing the reductant solution to flow in the direction of 90°.

TABLE 1

| Test example | Washing solution | Developing direction of washing solution | pH of washing solution | Concentration of washing solution component | Antigen | ΔOD | BG level | S/N |
|---|---|---|---|---|---|---|---|---|
| Example 1 | KI | 90° | 7 | 200 mmol/L | A+B– Flu Examan control, 1/5120 dilution | 0.126 | 0.099 | 20.1 |
| | | | | | None | 0.006 | 0.084 | |
| Example 2 | Urea | 90° | 7 | 200 mmol/L | A+B– Flu Examan control, 1/5120 dilution | 0.103 | 0.082 | 19.2 |
| | | | | | None | 0.005 | 0.058 | |

TABLE 1-continued

| Test example | Washing solution | Developing direction of washing solution | pH of washing solution | Concentration of washing solution component | Antigen | ΔOD | BG level | S/N |
|---|---|---|---|---|---|---|---|---|
| Example 3 | Guanidine | 90° | 7 | 200 mmol/L | A+B− Flu Examan control, 1/5120 dilution | 0.094 | 0.111 | 18.8 |
| | | | | | None | 0.005 | 0.107 | |
| Example 4 | KI | 0° | 7 | 200 mmol/L | A+B− Flu Examan control, 1/5120 dilution | 0.086 | 0.163 | 15.6 |
| | | | | | None | 0.006 | 0.153 | |
| Comparative example 1 | None | 90° | — | — | A+B− Flu Examan control, 1/5120 dilution | 0.067 | 0.198 | 9.8 |
| | | | | | None | 0.007 | 0.201 | |
| Comparative example 1 | Ultrapure water | 90° | 7 | — | A+B− Flu Examan control, 1/5120 dilution | 0.068 | 0.086 | 11.2 |
| | | | | | None | 0.006 | 0.077 | |
| Comparative example 3 | NaCl | 90° | 7 | 200 mmol/L | A+B− Flu Examan control, 1/5120 dilution | 0.107 | 0.104 | 4.1 |
| | | | | | None | 0.026 | 0.088 | |
| Comparative example 4 | KI | 90° (performing amplification by using mixed solution consisting of reductant solution and silver ion solution) | 7 | 200 mmol/L | A+B− Flu Examan control, 1/5120 dilution | 0.062 | 0.199 | 10.0 |
| | | | | | None | 0.006 | 0.185 | |

Next, the concentration of KI and urea in the washing solution was examined.

Example 5

Evaluation was performed in the same manner as in Example 1, except that the washing solution was replaced with a KI solution (50 mmol/L, pH 7).

Example 6

Evaluation was performed in the same manner as in Example 1, except that the washing solution was replaced with a KI solution (800 mmol/L, pH 7).

Example 7

Evaluation was performed in the same manner as in Example 1, except that the washing solution was replaced with a urea solution (50 mmol/L, pH 7).

Example 8

Evaluation was performed in the same manner as in Example 1, except that the washing solution was replaced with a urea solution (800 mmol/L, pH 7).

(Results of Examples 5 to 8)

Table 2 shows the results of Examples 1, 2, and 5 to 8. From Table 2, it was understood that when the concentration of the component in the washing solution is 50 mmol/L to 800 mmol/L, a high S/N ratio equal to or higher than 15 is obtained.

TABLE 2

| Test example | Washing solution | Direction of washing solution | pH of washing solution | Concentration of washing solution component | Antigen | ΔOD | BG level | S/N |
|---|---|---|---|---|---|---|---|---|
| Example 5 | KI | 90° | 7 | 50 mmol/L | A+B− Flu Examan control, 1/5120 dilution | 0.122 | 0.107 | 22.0 |
| | | | | | None | 0.006 | 0.100 | |

TABLE 2-continued

| Test example | Washing solution | Direction of washing solution | pH of washing solution | Concentration of washing solution component | Antigen | ΔOD | BG level | S/N |
|---|---|---|---|---|---|---|---|---|
| Example 1 | KI | 90° | 7 | 200 mmol/L | A+B− Flu Examan control, 1/5120 dilution | 0.126 | 0.099 | 20.1 |
|  |  |  |  |  | None | 0.006 | 0.084 |  |
| Example 6 | KI | 90° | 7 | 800 mmol/L | A+B− Flu Examan control, 1/5120 dilution | 0.141 | 0.102 | 28.8 |
|  |  |  |  |  | None | 0.005 | 0.128 |  |
| Example 7 | Urea | 90° | 7 | 50 mmol/L | A+B− Flu Examan control, 1/5120 dilution | 0.095 | 0.090 | 27.1 |
|  |  |  |  |  | None | 0.003 | 0.089 |  |
| Example 2 | Urea | 90° | 7 | 200 mmol/L | A+B− Flu Examan control, 1/5120 dilution | 0.103 | 0.082 | 19.2 |
|  |  |  |  |  | None | 0.005 | 0.058 |  |
| Example 8 | Urea | 90° | 7 | 800 mmol/L | A+B− Flu Examan control, 1/5120 dilution | 0.095 | 0.090 | 22.8 |
|  |  |  |  |  | None | 0.004 | 0.076 |  |

This application claims priority under 35 U.S.C. §119 of Japanese Patent application JP 2013-068503, filed on Mar. 28, 2013 and Japanese Patent application JP 2014-038232, filed on Feb. 28, 2014, the entire contents of which are hereby incorporated by reference.

What is claimed is:

1. A chromatography method comprising:
   (a) developing a complex of a test substance and a labeling substance modified with a first binding substance which specifically binds to the test substance, onto an insoluble carrier;
   (b) causing the complex to be trapped in a reaction site on the insoluble carrier, wherein the reaction site contains a second binding substance which specifically binds to the test substance or contains a substance which specifically binds to the first binding substance;
   (c) washing the insoluble carrier with a washing solution containing potassium iodide after the step (b), wherein the concentration of potassium iodide in the washing solution ranges from 50 mmol/L to 800 mmol/L and the washing solution has a pH of 5-8;
   (d) washing off the washing solution remaining on the insoluble carrier from the insoluble carrier; and
   (e) amplifying the labeling substance of the complex trapped in the reaction site, wherein in the step (d), a first amplification solution containing a reductant capable of reducing silver ion is used to wash off the washing solution from the insoluble carrier, and in the step (e), a second amplification solution containing a silver ion-containing compound is used to amplify the labeling substance of the complex.

2. The chromatography method according to claim 1, wherein in the step (c), the amount of the potassium iodide applied to the insoluble carrier is 0.8 μg/mm$^2$ to 300 μg/mm$^2$, and
   wherein the applying was in the washing solution in the step (c).

3. The chromatography method according to claim 1, wherein the washing solution of the step (c) is made to flow, forming an angle of 45° to 135° with respect to the developing direction of the test substance.

4. The chromatography method according to claim 1, wherein the first amplification solution is made to flow, forming an angle of 45° to 135° with respect to the developing direction of the test substance.

5. The chromatography method according to claim 1, wherein the labeling substance is metal colloid.

6. The chromatography method according to claim 5, wherein the metal of the metal colloid is gold, silver, platinum, or palladium.

7. The chromatography method according to claim 1, wherein the reductant capable of reducing silver ion is $Fe^{2+}$.

* * * * *